(12) United States Patent
Hofmann et al.

(10) Patent No.: US 7,854,844 B2
(45) Date of Patent: *Dec. 21, 2010

(54) DETECTION SYSTEMS AND METHODS

(75) Inventors: Martin John Hofmann, Gloucestershire (GB); David Johnson, Gloucestershire (GB)

(73) Assignee: Pall Corporation, Port Washington, NY (US)

(*) Notice: Subject to any disclaimer, the term of this patent is extended or adjusted under 35 U.S.C. 154(b) by 882 days.

This patent is subject to a terminal disclaimer.

(21) Appl. No.: 11/678,236

(22) Filed: Feb. 23, 2007

(65) Prior Publication Data
US 2007/0138100 A1    Jun. 21, 2007

Related U.S. Application Data

(62) Division of application No. 10/496,940, filed as application No. PCT/GB02/05333 on Nov. 27, 2002, now Pat. No. 7,195,709.

(30) Foreign Application Priority Data

| Nov. 27, 2001 | (GB) | ................... 0128464.5 |
| Nov. 29, 2001 | (GB) | ................... 0128677.2 |
| May 3, 2002 | (GB) | ................... 0210220.0 |

(51) Int. Cl.
*B01D 15/08* (2006.01)
(52) U.S. Cl. .................... 210/635; 210/656; 210/198.2; 422/70; 436/161
(58) Field of Classification Search ................ 210/635, 210/656, 96.1, 198.2; 141/12, 80; 422/70; 436/161
See application file for complete search history.

(56) References Cited

U.S. PATENT DOCUMENTS

| 3,706,381 | A | * | 12/1972 | Joynes et al. ............. 210/198.2 |
| 4,324,131 | A | | 4/1982 | Rosencwaig |
| 4,919,804 | A | | 4/1990 | Dorsey et al. |
| 5,061,371 | A | | 10/1991 | Tabata et al. |
| 5,646,048 | A | | 7/1997 | Templin et al. |
| 5,708,191 | A | | 1/1998 | Greenwood et al. |
| 5,770,087 | A | | 6/1998 | Reuter |
| 5,886,250 | A | | 3/1999 | Greenwood et al. |
| 6,082,180 | A | | 7/2000 | Greenwood |

(Continued)

FOREIGN PATENT DOCUMENTS

GB    1 312 096    4/1973

(Continued)

OTHER PUBLICATIONS

Greenwood, M. S., et al., *Journal of Fluids Engineering*, 126(2):189-192 (2004).

*Primary Examiner*—Ernest G Therkorn
(74) *Attorney, Agent, or Firm*—Leydig, Voit & Mayer, Ltd.

(57) ABSTRACT

The application describes apparatus and methods using ultrasound transmitted through a chromatography column bed to determine the status of materials in the bed space, particularly during chromatography runs. Detected conditions include the profile of a band of eluting material—to see whether it is satisfactory—the arrival of a band of material at the column output, the fitness for use of the ed packing, the passage of different mobile phases, e.g. salt fronts, and other conditions. Aspects claimed include control processors and corresponding programmed products.

12 Claims, 12 Drawing Sheets

U.S. PATENT DOCUMENTS

| | | |
|---|---|---|
| 6,082,181 A | 7/2000 | Greenwood |
| 6,763,698 B2 | 7/2004 | Greenwood |
| 6,868,715 B1 * | 3/2005 | Carnahan et al. ........... 73/64.54 |
| 6,877,375 B2 | 4/2005 | Greenwood |
| 6,966,991 B2 | 11/2005 | Hofmann |
| 7,195,709 B2 * | 3/2007 | Hofmann et al. ......... 210/198.2 |
| 7,279,094 B2 * | 10/2007 | Hofmann ................. 210/198.2 |
| 2003/0089662 A1 | 5/2003 | Hofmann |

FOREIGN PATENT DOCUMENTS

| | | |
|---|---|---|
| GB | 2 167 185 | 5/1986 |
| WO | WO 02/10739 | 2/2002 |

\* cited by examiner

1st run of loading and elution of MABS

1st run of loading and elution of MABS blank run to show ultrasound interface of wash buffer and equilibration buffer FIG. 14
FIG. 15
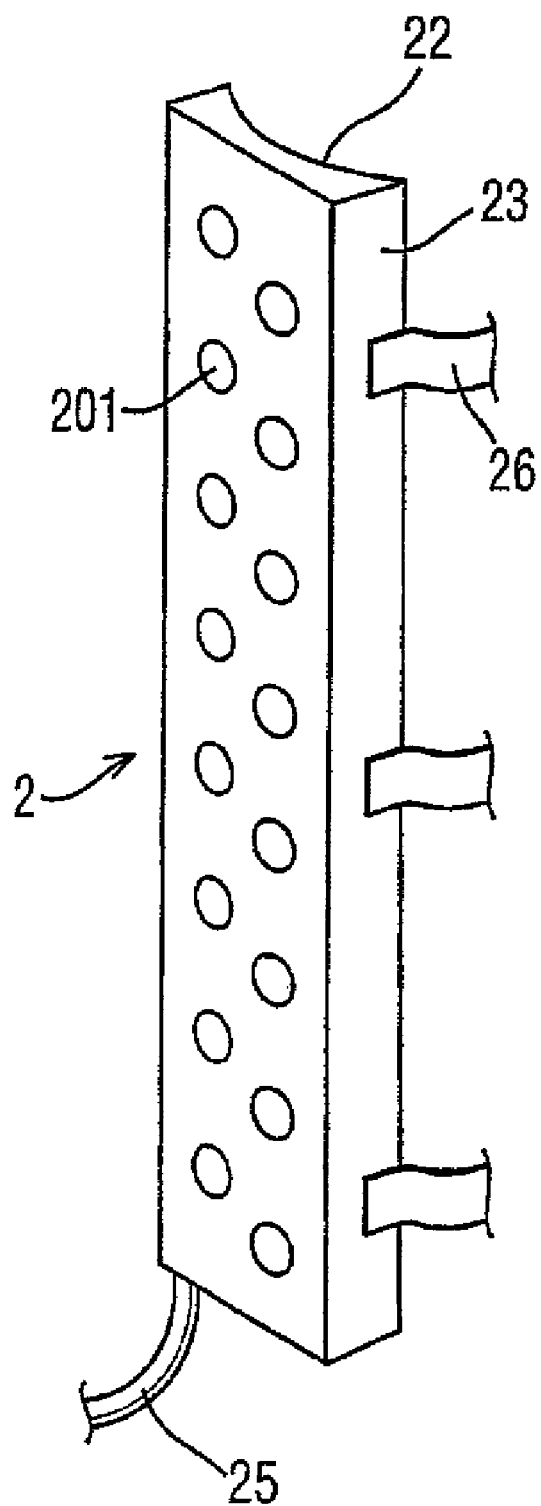
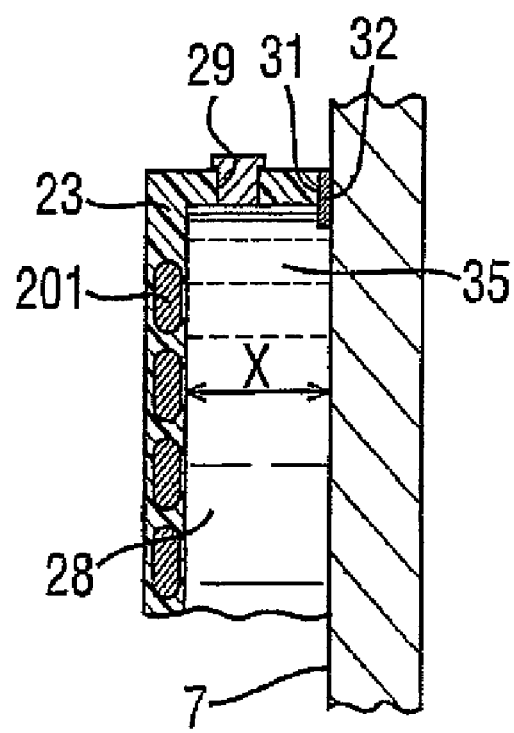

DETECTION SYSTEMS AND METHODS

REFERENCE TO RELATED APPLICATIONS

This application is division of Ser. No. 10/496,940, now U.S. Pat. No. 7,195,709, which, in turn, is a 371 of PCT/GB02/05333 filed Nov. 27, 2002.

FIELD OF THE INVENTION

This invention relates to detection systems and methods used in the field of chromatography, and to apparatus and methods for chromatography incorporating such detection systems and methods. Chromatography is the separation—often for purposes of purification—of components in a mixture by passing them with an eluent liquid through a bed of particles.

BACKGROUND

It is normal for various detectors to be present in the piping systems associated with a chromatography column, either immediately adjacent or on the column, or in associated machinery such as packing skids which may from time to time be connected to the column. For example it is normal for the outflow from the column to include a pH meter and/or a UV monitor, the latter detecting the presence of chemical species in the outflow which have UV-absorptive chromophores. Normally a pressure gauge is connected to the column interior or pumping system.

In the prior-published art, U.S. Pat. No. 4,324,131 describes using a ultrasonic detector to detect solutes in the effluent liquid from a chromatography column; only schematic details are given but essentially ultrasound is passed through a cell through which the effluent passes and a second, control cell containing pure eluent; differences in the transmitted ultrasound amplitude indicate dissolved substances.

Our earlier but not prior-published WO 02/10739, the contents of which are hereby incorporated by reference, describes a different mode of use of ultrasound in relation to chromatography columns and processes. It is disclosed that vibratory transmissions, especially ultrasound, can pass right across the packed column interior and indicate the situation within. A particular aspect is showing the presence of absence of packed bed material (medium); various methods and apparatus are disclosed for using ultrasound arrangements to monitor and control the packing of a column. It was also found that the ultrasound transmissions can detect the presence of additional substances in the column, in particular bands of eluted components passing through, and bound impurities or other components remaining in a band on the media so as to affect the ultrasound transmission.

THE INVENTION

The present application proposes further developments and refinements of the proposals disclosed in WO 02/10739, with particular but not exclusive reference to the use of mechanical vibratory transmissions and especially ultrasound to detect adventitious material in the column bed, particularly component(s) being separated or purified but also material which may be temporarily or permanently fixed—bound or physically retained—on the medium particles in the column. Also, methods in which the transmissions are used to detect in-column phenomena associated with process runs but not necessarily involving eluted components as such.

Some aspects of the invention are set out in the claims.

In one novel aspect we have found that, as a given substance elutes through the column across a signal transmission path, the resulting profile of modification (attenuation or speed change) of the mechanical vibratory transmission e.g. ultrasound is to some extent distinctive, i.e. can be used to distinguish a band of a given component from a band of at least one other different component that might be present with it, or from an improperly-eluting band of the same component.

The exact reasons for the form of these distinctive transmission modification profiles are of course complex. They relate to details of the interactions between the eluting component, the particulate bed medium and the eluent. They may reflect the presence of near-identical substances e.g. isomers and variants eluting together through the bed at slightly different rates. Whatever the reasons, we have found that in practice different substances e.g. different proteins can give characteristic traces.

It is possible that the temperature of the bed varies slightly on absorption and desorption of the eluting substance on and off the media particles. This has the potential to modify the transmission because the present techniques allow changes in the column to influence the transmission over a very long path length; twice the transverse dimension of the column which for many industrial-scale columns will give a path length of a metre or more. However this is one theory and we are not bound to it.

We do note that, where the present technique is used to detect band profiles which are also UV-absorptive on leaving the column, there are similarities in the band profiles between the two techniques and this is more readily understood as corresponding to the spreading of peaks into distinct sub-peaks e.g. because of isomeric forms eluting at slightly different rates. However the present ultrasound transmissions (henceforth the term "ultrasound" used in the present statements of the invention refers generically to acoustic or mechanical vibratory transmissions unless the context requires otherwise) can detect the component when it is inside the column, whereas UV requires a transparent path outside the column. Thus, the detection monitoring is available throughout the process including important on-column stages, also for substances which do not absorb UV light.

Also, the purity of a sample may be calculated from the ratio of the sizes of peaks in its ultrasound profile. This is a known technique in UV spectroscopy, but has not previously been used with ultrasound. A control processor may be programmed accordingly, or the data interpreted visually by an operator.

Preferably the detection technique monitors the amplitude/attenuation of the transmitted ultrasound rather than speed changes, because the latter are found rather sensitive to temperature which may be disadvantageous in many cases.

In one general apparatus aspect, the present invention relates to the provision and use of a control processor in relation to a chromatography apparatus comprising a chromatography column having a housing wall with side wall and end portions defining an internal bed space for containing a particulate chromatography medium, and having at least one transmitter for transmitting a vibratory mechanical signal such as ultrasound through the bed space, and at least one detector to detect the transmitted signal(s).

In a first aspect the control processor is programmed to compare a transmission profile observed in the course of a chromatography process with a model transmission profile for a component of interest, and determine future processing conditions or information provided to the user on the basis of the comparison. It may additionally cause an image or trace of the profile to be displayed (this is disclosed in our earlier application). In particular, the control processor—which may be a programmable logic controller (plc) or a pc—may initiate a warning if the comparison indicates a mismatch between an actual detected profile and a predetermined model profile for a given component. The revealing of significant differences, for example serious tailing or spreading of the profile, or much smaller than predicted area under the profile peak indicating lack of product, can be used as an indication of a faulty process perhaps long before the substance reaches the column outlet. The fault might arise because of a fault in the bed, an improperly loaded sampler or some fault in the preparation of the sample. This early check enables a run to be terminated early if things are not going properly, potentially avoiding significant wasted time and cost.

The control processor may additionally or alternatively be programmed to initiate the operation of one or more system valves acting on effluent from the column, e.g. switching output from the column from a waste output line to a sample collection output line, in dependence on the impending arrival at the column outlet, predicted by the detected ultrasound transmission on the column, of a band of an eluted target component. By tracking progress of the band before it arrives at the outlet, more accurate timing is achievable and "tighter cuts" than by using UV alone, downstream of the outlet. This process may or may not involve the comparison of the profile with a model profile as proposed above. Additionally or alternatively, the control processor may simply initiate a warning signal in dependence on the impending arrival of a component at the column outlet detected as described.

Where appropriate, stored data representing model component profiles under the appropriate conditions may be provided on removable data carriers e.g. magnetic cards or disks which can be read by the control processor or by a reader associated with it.

In a preferred arrangement, the chromatography apparatus provides a series of transmission paths distributed axially along the chromatography column, e.g. by means of an array of transmitters and/or sensors, and data are gathered by periodically taking a set of readings over the set of paths in a short period, e.g. as a "scan" up or down the whole or a selected part of the column. Preferably at least 5, more preferably at least 10 or at least 15 sensors are used.

The periodicity of the multi-path scan is not critical and may be suited to the process in hand. This technique is appropriate for all on-column applications of ultrasound, incidentally, and not restricted to those detecting eluting bands of product.

Ultrasound detection may be used with a wide variety of eluting molecules, from simple small molecules—which may include solvent molecules—through larger molecules to linear and globular molecules such as proteins and globulins, for example immunoglobulins which may be for example monoclonal antibodies. These are high-value products in biochemical processing and we find that our ultrasound techniques detect them well.

Interestingly, the ultrasound methodology enables detection of some events to which conventional spectroscopy e.g. UV would be blind, even if it could see into the column. In particular, the ultrasound is sensitive to changes of pressure or compression in the column. Thus, it can be seen from an ultrasound trace of a run when the column is switched offline. It can also be seen where the eluent e.g. eluting buffer is changed, for example to wash from the column components which previously were bound. Without being committed to the theory, this may be because different eluent liquids have different viscosities, so that they compress the bed to varying degrees as they are pumped through. The ultrasound record of a run showing such events is a valuable diagnostic tool.

Another valuable tool is to indicate the base line change relative to the "clean" medium before the first run. Successive runs progressively accumulate bound material on the media particles which may not all be able to be washed off. Acceptable threshold levels of such bound material may be determined and an initial ultrasound check or scan of the bed used to check whether the base line binding is acceptable. Our earlier application disclosed this for a band of impurity at the input side of the column. It is disclosed here in relation to the column as a whole, or to parts of the bed spaced away from the input.

The ultrasound technique may provide new and useful ways of testing the purification procedures used as well as the purity of the products themselves. Ultrasound can be used to check the purity and concentration of the sample as outlined above, or it can be used to test the 'goodness' of the pack without the need (as is conventional) to pass a test chemical (e.g. salt or acetone) through the column. The ultrasound may be able to look at a pack directly to assess how well it is packed. This is desirable given the cost of such media; the ability to produce a tested, yet unused, column may be a commercial advantage.

A further use benefit in is in being able to see while still on the column when (where, axially) given components become effectively resolved. In pilot stages this enables a rapid determination as to the length of bed required for resolving given components under given conditions.

A further aspect relates to a sensor array. Because of the usefulness of the technique and its applicability to existing columns, a preferred aspect of the invention is an array of ultrasound sensors (transmitters and/or detectors) configured to be secured in an operating position against the side wall of a chromatography column, by means of fastening means which are preferably integrally joined to the array, and which is releasable so that the array can be transferred from one column to another. The array of ultrasound sensors preferably has an electrical connector for the sensors which can readily be disconnected e.g. unplugged, e.g. as a single cable, for connection to different control processors. Or, it may be integrally (permanently) joined to a given control processor. The ultrasound array is preferably a single array of transceivers, although complementary arrays of transmitters and detectors may be used instead. The array device may have a concave front face shaped for conformity with a column side wall. In one preferred embodiment the transmitter-mounting element has a front recess which is closed off by the column wall to form a fluid chamber to hold a contact fluid; this has been found to facilitate calibrating and zeroing of multiple transmitters, which otherwise are very difficult to bring into precisely matched contact with the solid column wall.

We prefer to provide control units for the column packing operation (described in our earlier application) and the column running operation (such as described herein) separately, because it is not normally preferred to keep pumping skids etc. near the column during a run. So, in a preferred aspect a control unit having the run processing features described herein or in the earlier application does not include any packing pump control programming, or the control apparatus does not include any packing pump or pump connections, or is not adapted for pumping packing material. Or, any combination of these absences.

A further aspect of the invention is a computer program product or programmable logic controller, embodying software code which, when run, carries out any one or more of the control processing functions described herein.

Finally, we have noted that the ultrasound methods and apparatus proposed herein and in our earlier application are useful not only on close-packed but also in loose-packed beds, particularly beds which are expanded in use in so called expanded-bed chromatography processes. Because the effect on the ultrasound transmission is heavily dependent on the closeness of packing/compression of particles in the bed space, the system may be used in an expanded bed process to indicate the degree of expansion of the particles within. This is a valuable facility because for a given process there are normally optimal degrees of expansion of the bed.

BRIEF DESCRIPTION OF THE DRAWINGS

Experiments, methods and apparatuses explaining and illustrating the invention and embodiments of it now follow, with reference to the accompanying drawings in which:

FIG. 14 is a perspective partial view illustrating a detachable multi-sensor array, and FIG. 15 is a fragmentary view of part of a multi-sensor array adapted to form a fluid chamber.

FIG. 1 shows a pilot set-up for transmitting ultrasound across a chromatography column; a commercially available piezoelectric transceiver is clamped against the column wall which here is a transparent polymeric wall enabling visual cross-reference of conditions. This apparatus is used in the IgG experiment later on.

FIGS. 2 and 3 illustrate the behaviour of ultrasound transmissions across the bed space. Essentially, ultrasound is reflected at interfaces between materials of differing densities. There is an immediate reflection (peak P) from the wall immediately adjacent the transducer. Then, after a time corresponding to the time for the ultrasound to cross the bed space and back again, there are reflected signals Q, R bouncing respectively from the inner and outer surfaces of the opposite wall. The control software is programmed to work with the opposite inner wall signal Q.

FIG. 3 shows how some intervening discontinuity can be "seen" by the ultrasound: a flaw created in the centre of the bed shows up as an intervening peak S. This peak was seen to disappear as buffer was passed over time, gradually resolving the flaw.

Experiment 1

In experimental work, we prepared a 400 mm diameter column 200 mm long, loaded with Sepharose 4FF gel. In this work we monitored the amplitude attenuation of the ultrasound transmission along a single transmission path halfway down the column.

Figure 4:
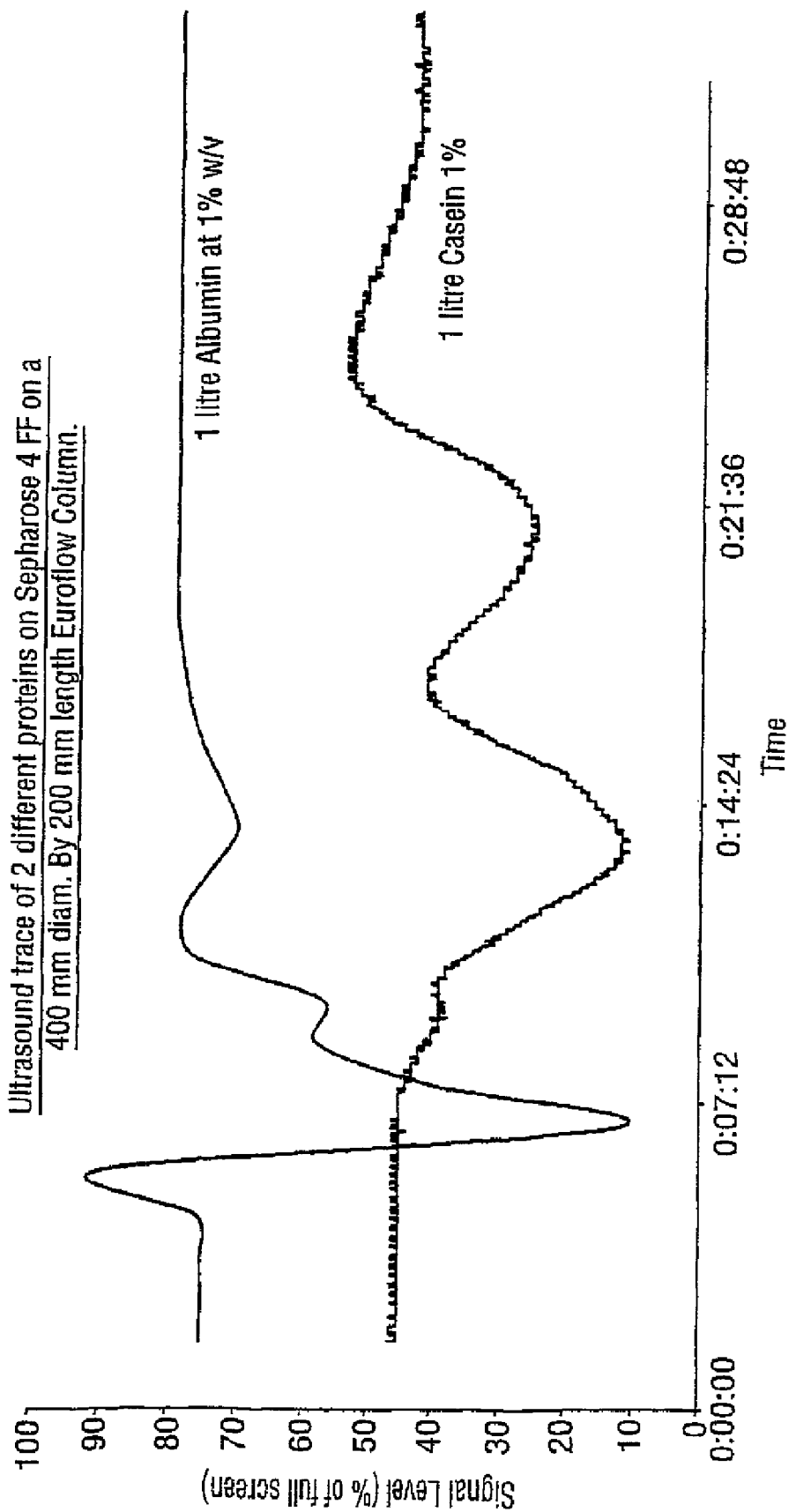
FIG. 4 is an ultrasound trace over time showing the detection of different proteins eluting through a column.

The mobile phase was water. With the column stable, one litre of 1% w/v albumin in water was applied to the column. The resulting ultrasound trace (x axis time, y axis transmitted signal amplitude) is shown in the upper part of FIG. 4. It shows a particular peak profile for the passage of the albumin band across the detected ultrasound transmission path. Repeated injections of albumin gave profiles of the same shape.

Then, one litre of 1% casein in water was applied to the column and passed at the same rate. The resulting ultrasound trace is seen in the lower part of FIG. 4. There has been some baseline shift relative to the albumin run, but the peak profile for the casein was reproducible. Furthermore it was clearly distinct from the albumin peak profile. Without wishing to be bound by theory, it may be that various slightly different forms of casein in the sample eluted at slightly different rates, leading to the characteristic profile.

The person skilled in the design of electronic process control apparatus will readily appreciate that these profiles can be stored in machine-readable electronic or magnetic form, e.g. on a card or disk, or in a PC or PLC (programmable logic controller) and that a control processor can readily be programmed to compare profiles measured in real time against the stored profiles by means of appropriate "goodness of fit" mathematical tests. According to criteria which can be determined empirically, with reference to chromatography runs using known materials and with successful results, these comparisons can then be used for the useful purposes described above.

Experiment 2

Figure 5:
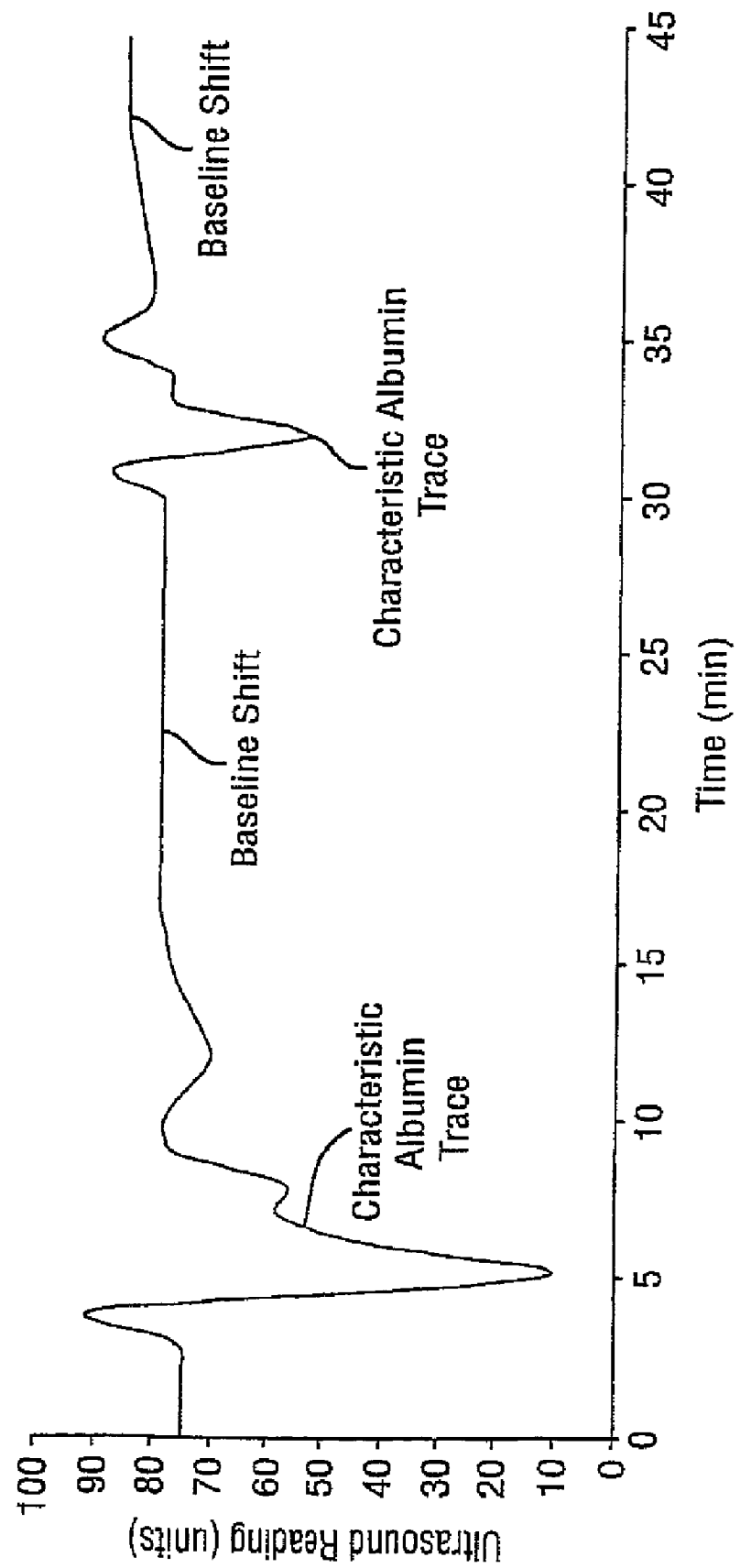
FIG. 5 is a trace for two passes of different amounts of the same protein (egg albumin) showing characteristic features.

In a further experiment, two injections of albumin (first 1 l and then 0.5 l of the same 10 g/l solution) were made successively into a column running under the same conditions. FIG. 5 shows the resulting trace. This shows firstly the reproduction of the characteristic trace profile for albumin. Secondly it shows a shifting of the transmission baseline following each successive injection. This appears to be attributable to the progressive retention of a certain amount of sample on the bed medium, and therefore shows that in general the present system may also detect ongoing levels of "fouling" of the column. Thus, practical threshold levels of fouling may be correlated by testing with "baseline" transmission levels, and the system then programmed on the basis of the correlation to give an indication of the level of fouling and/or a warning as to when a threshold level is reached or approached.

Experiment 3

In this experiment, a mammalian cell culture in a 500-litre fermenter was used to biosynthesise a monoclonal antibody Immunoglobulin G (IgG). The cell culture supernatant was filtered and two runs totaling 85 g IgG in 200 litres of this filtered liquid was purified on a 180 mm diameter by 150 mm bed height, 4FF-Sepharose Protein A chromatography column. An ultrasound monitor was placed at the base of the column and the changes in ultrasound signal were recorded during 2 process runs. A blank run was also carried out to reveal the effect of buffer changes on ultrasound signals. The blank was subtracted from the test to confirm which peak was the IgG peak, similar to a 'spike' experiment.

The experiment was carried out using a mammalian cell culture; Lonza's strain 6A1(100)3. It was fermented in a 500 litre stirred tank fermenter. At the end of the fermentation the cells die and release their IgG; the IgG being designated B72.3.

After fermentation the fermentation liquor was disc stack centrifuged giving the primary recovery liquid. This was then microfiltered through a 'Cuno' depth filter then sterile filtered through a Millipore PVDF 0.2 um filter to yield the 200 litre yellow liquid for chromatography. This liquid contained 0.425 g IgG/litre or in the total 200 litres, 85 g of IgG.

A 180 mm diameter Moduline II glass column was packed to 150 mm bed height with rmp Protein A Sepharose 4 Fast Flow, this being 3.82 litre. The recombinant (rmp) Protein A (from *E. coli*) from Amersham Biosciences ("APB") is designed for therapeutic applications that require extremely pure eluates. The rmp Protein A has an r.m.m. of 44.6 kd and contains five antigen binding domains. On average a single rmp Protein A molecule can bind two antibody molecules. The binding capacity of the media at 200 cm/hr is about 15 mg IgG/ml of media (see published APB datafile 18-1141-34 AA, 2000-01).

An Amersham BioProcess System (no. 1357) was used to dilute and supply buffers and samples to the column and to collect the fractions. This chromatograph had eight buffer inlet ports (switchable) two pumps, 8 pump heads, pre-column conductivity and pressure, bubble trap and filter (by-passable), valves to change column flow direction and by-pass; post column conductivity, pH, flow and UV spectrometer. The data from the sensors was logged to a PC.

The Tables below itemise the chromatography steps performed in the two experimental runs.

TABLE 1 showing Run 1: Chromatography Conditions used to Separate IgG from Clarified Cell Supernatant

| Step | Mobile Phase (150 cm/hr; 640 ml/min) | Purpose | Column Volumes |
|---|---|---|---|
| 1 | 6M Guanidine HCl (aq., pH ca.4.6) | To clean the column prior to process | 8 |
| 2 | 0.05M Glycine-Glycinate (pH 8.4) | Equilibrium buffer | 10 |
| 3 | Clarified process sample | Load | 16 (62 l) |
| 4 | 0.05M Glycine-Glycinate (pH 8.4) | Wash | 10 |
| 5 | 0.1M Glycine (HCl) (pH 3.5) | Elute IgG | 3 |
| 6 | 0.1M Citric Acid (pH 2.1) | Regeneration (strip) | 2 |

TABLE 2 showing Run 2: Chromatography Conditions used to Separate IgG from Clarified Cell Supernatant

| Step | Mobile Phase (150 cm/hr; 640 ml/min + some variations) | Purpose | Column Volumes |
|---|---|---|---|
| 1 | 6M Guanidine HCl (aq., pH ca.4.6) | To clean the column prior to process | 8 |
| 2 | 0.05M Glycine-Glycinate (pH 8.4) | Equilibrium buffer | 10 |
| 3 | Clarified process sample | Load | 36 (138 l) |
| 4 | 0.05M Glycine-Glycinate (pH 8.4) | Wash | 10 |
| 5 | 0.1M Glycine (HCl) (pH 3.5) | Elute IgG | 3 |
| 6 | 0.1M Citric Acid (pH 2.1) | Regeneration (strip) | 2 |

Figure 1:
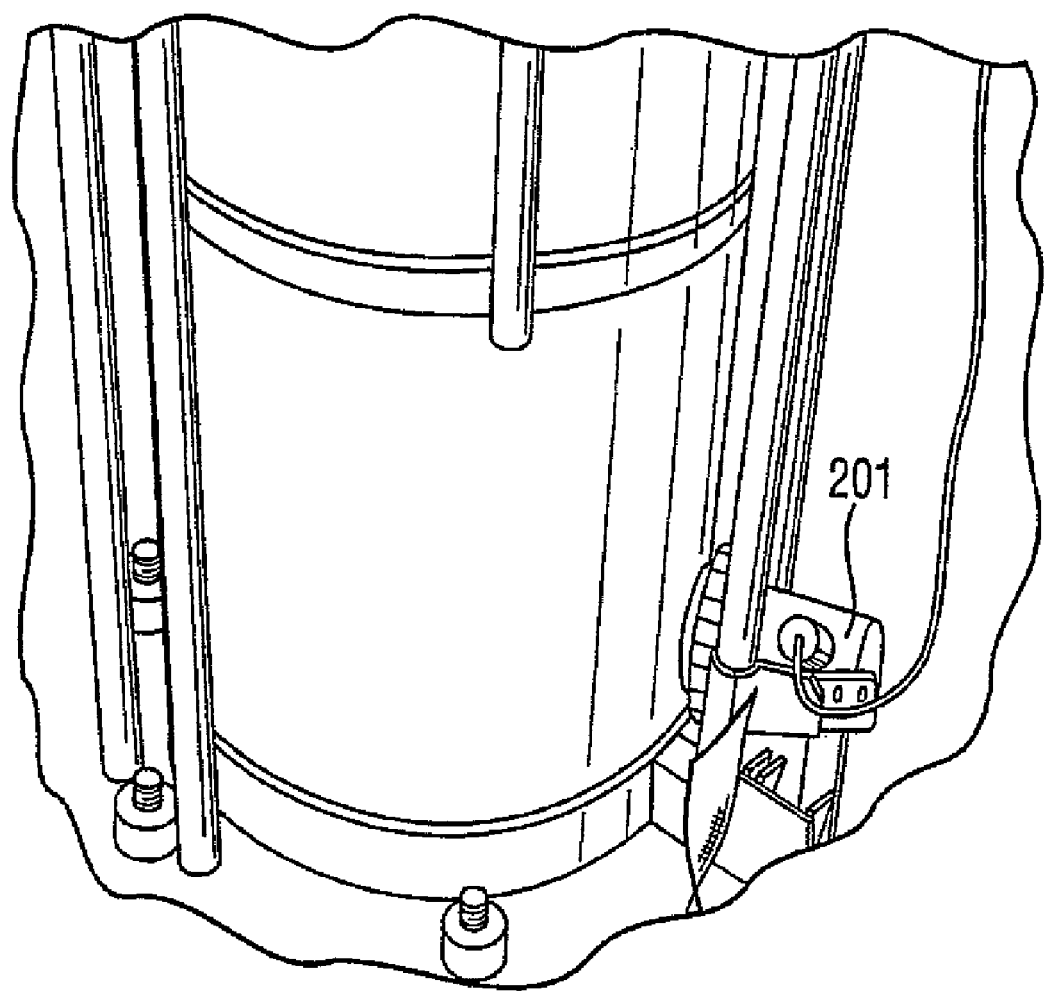
FIG. 1 shows a chromatography column with a single ultrasound transceiver installed.
Figure 2:
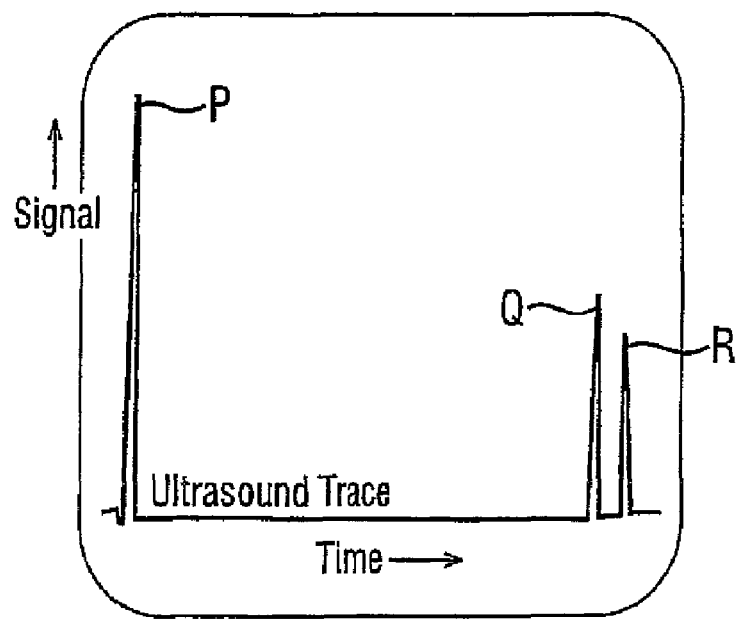
FIG. 2 shows the typical nature of a received ultrasound signal.
Figure 3:
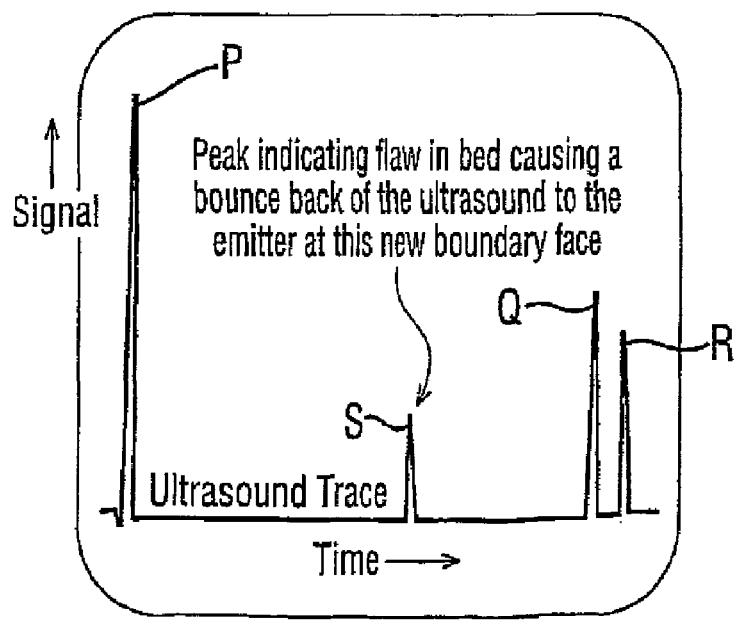
FIG. 3 resembles FIG. 2 but showing the detection of a bed fault.

A single 1 MHz transducer was placed at the base of the column, as shown in FIG. 1. In this position the ultrasound signal would 'sense' conditions at the portion of the column bed near the outlet.

FIG. 1 shows the position of the ultrasound transducer clamped at the bottom-right of the column. This picture also shows the process liquid added at the top of the bed. Note that the bed was compressed as the sample was applied due to its higher viscosity. This change in bed height caused a change in the ultrasound signal. Such changes in ultrasound signal occurred also when high salt plugs were applied to the top of the column in other experiments on this column.

Figure 6:
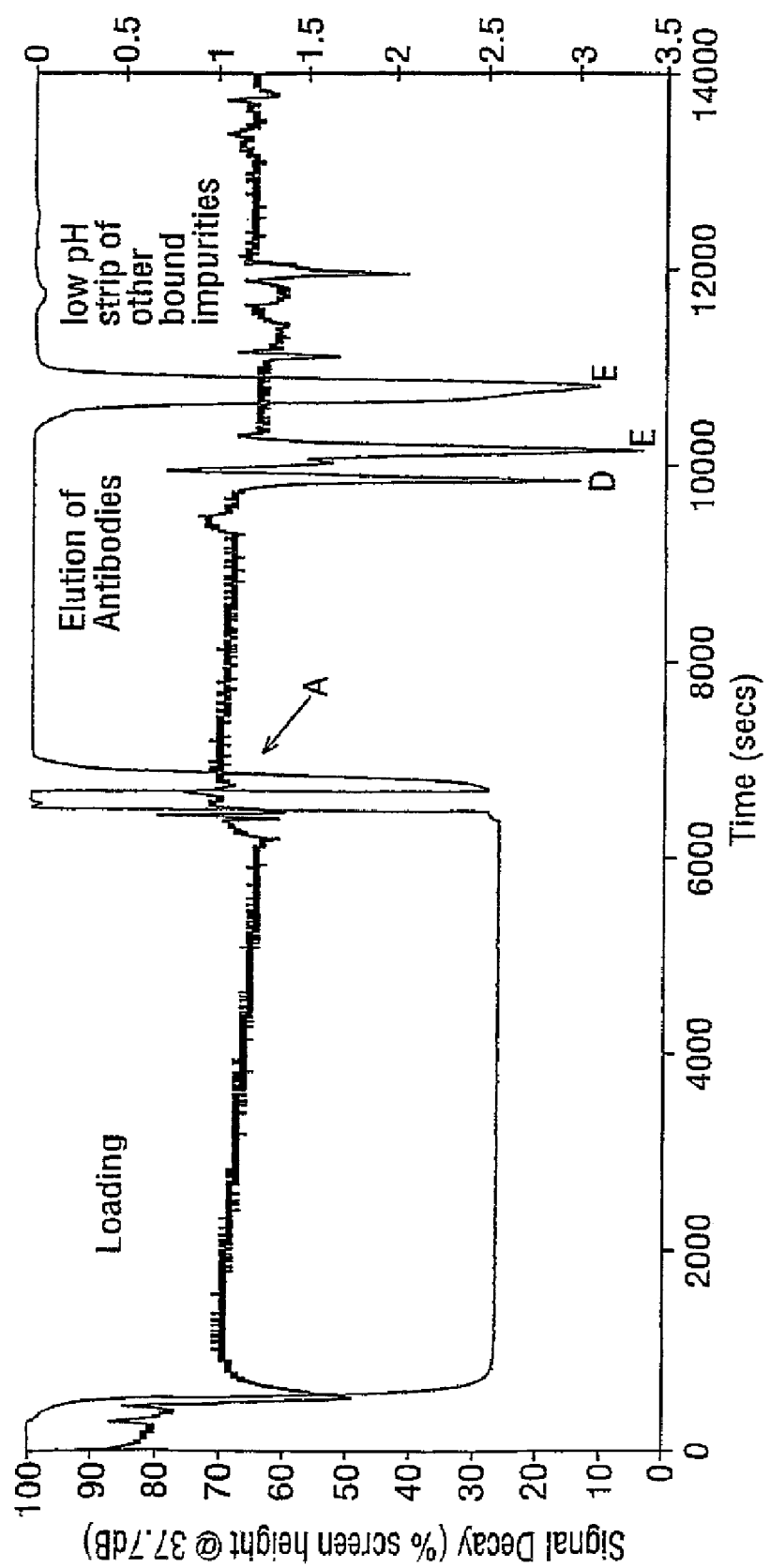
FIGS. 6 to 10 show readings during elution of a monoclonal IgG on the FIG. 1 column, partly supplemented with UV readings.

FIG. 6 shows the ultrasound readings for the entire run. During loading the signal strength reduced over time. This is due to the gradually increasing loading of the protein A on the medium, making for more attenuative conditions. The UV (top thin trace) is constant because it is monitoring a dynamic flow situation, where a more or less constant amount of material is immobilised from the stream whilst flowing through the column. This makes the UV essentially blind to what is happening inside the column and the first indication of the column being fully loaded is the UV going off scale. With the ultrasound we have a view of the degree and extent of loading throughout the column, if >1 transceiver is used, rather than a column-wide average given by the media manufacturers. This will allow more efficient loading of a column.

After loading, the column is washed to remove as much un-bound impurity as possible; this can be seen coming off as a tight band A on FIG. 6. Both the UV and ultrasound could see this. On closer inspection the ultrasound peak is seen before the UV peak. Because of the tightness of this peak versus the dimensions of the transducer it is expected that a smaller transducer would resolve the peak much more clearly. The ultrasound signal levels off after the initial large peak indicating that bound species are left on the column, requiring a further pH change to remove them.

Figure 7:
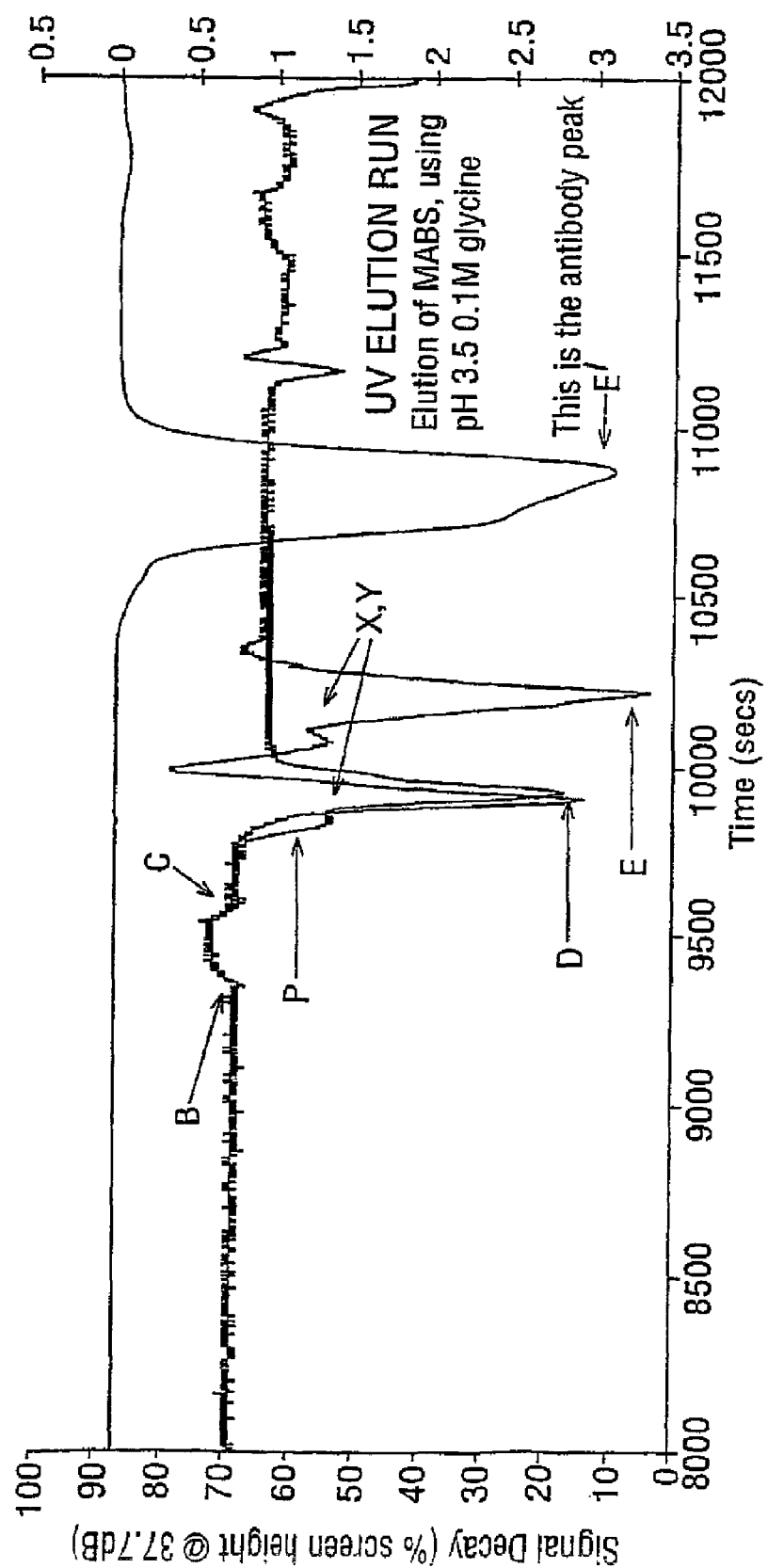

FIG. 7 shows the trace in more detail from the end of the loading phase. Point B shows the column bed relaxing as the column is taken off-line, when the column is put back on-line when the system is full of elution buffer the bed can be seen to compress again at C. This is where the blank trace P is overlaid i.e. a trace from a corresponding run where a buffer change was performed on an unloaded bed, so that the antibody trace could be conclusively separated from the background. The antibody peak E in the true run can be clearly seen as separate and coming after the buffer exchange peak D. Between the peaks there is evidence that there is a strong interface between the antibody band and the preceding buffer exchange interface. The UV antibody peak E' comes off significantly after the ultrasound peak, and they both have much the same morphology.

The shoulders X, Y that are present on the front flank of the blank trace and the front flank of the antibody trace appear to be miniature buffer exchange interfaces. After the peaks have come off, the trace returns to the stable level of the elution buffer, which is slightly less than that of the equilibration buffer.

Figure 8:
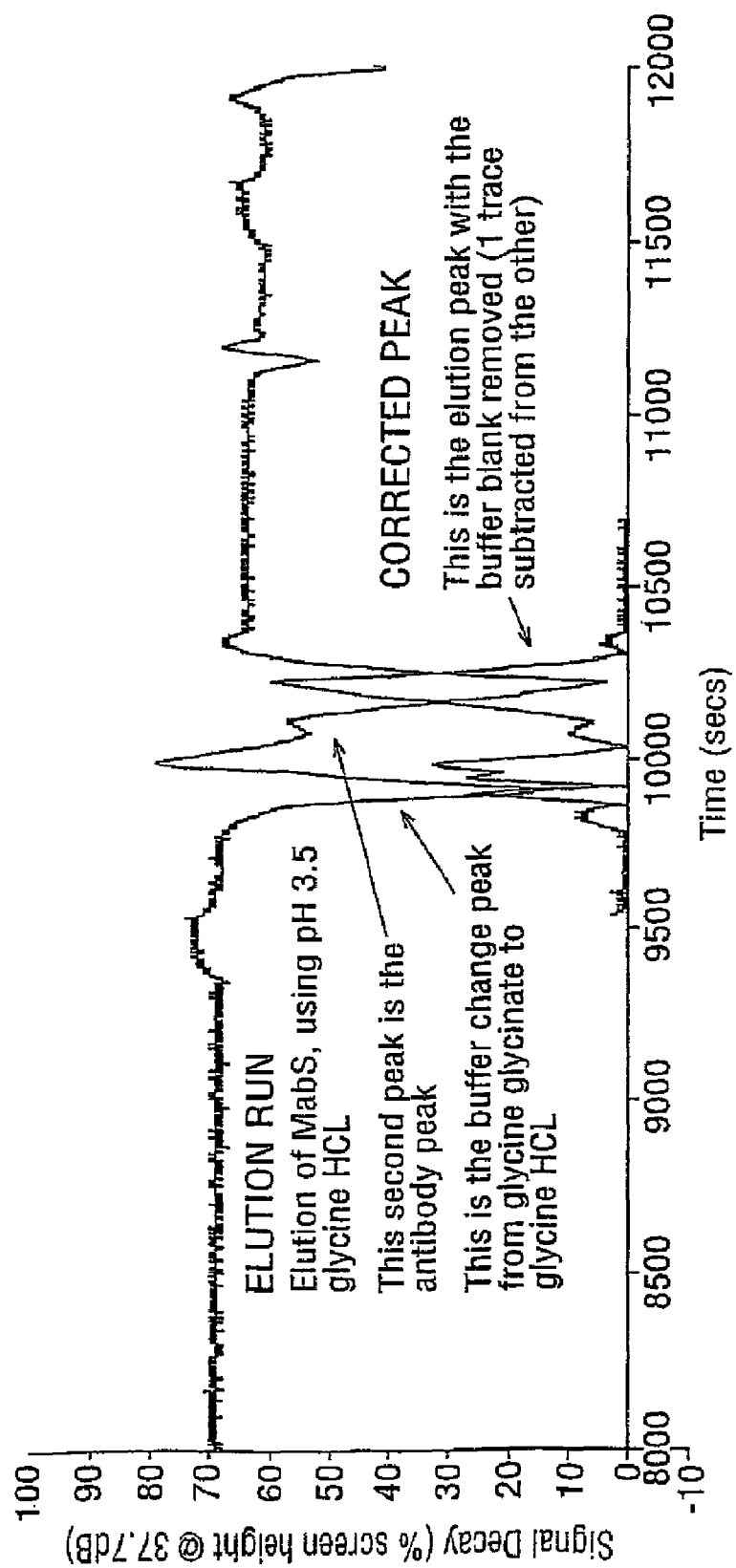
Figure 9:
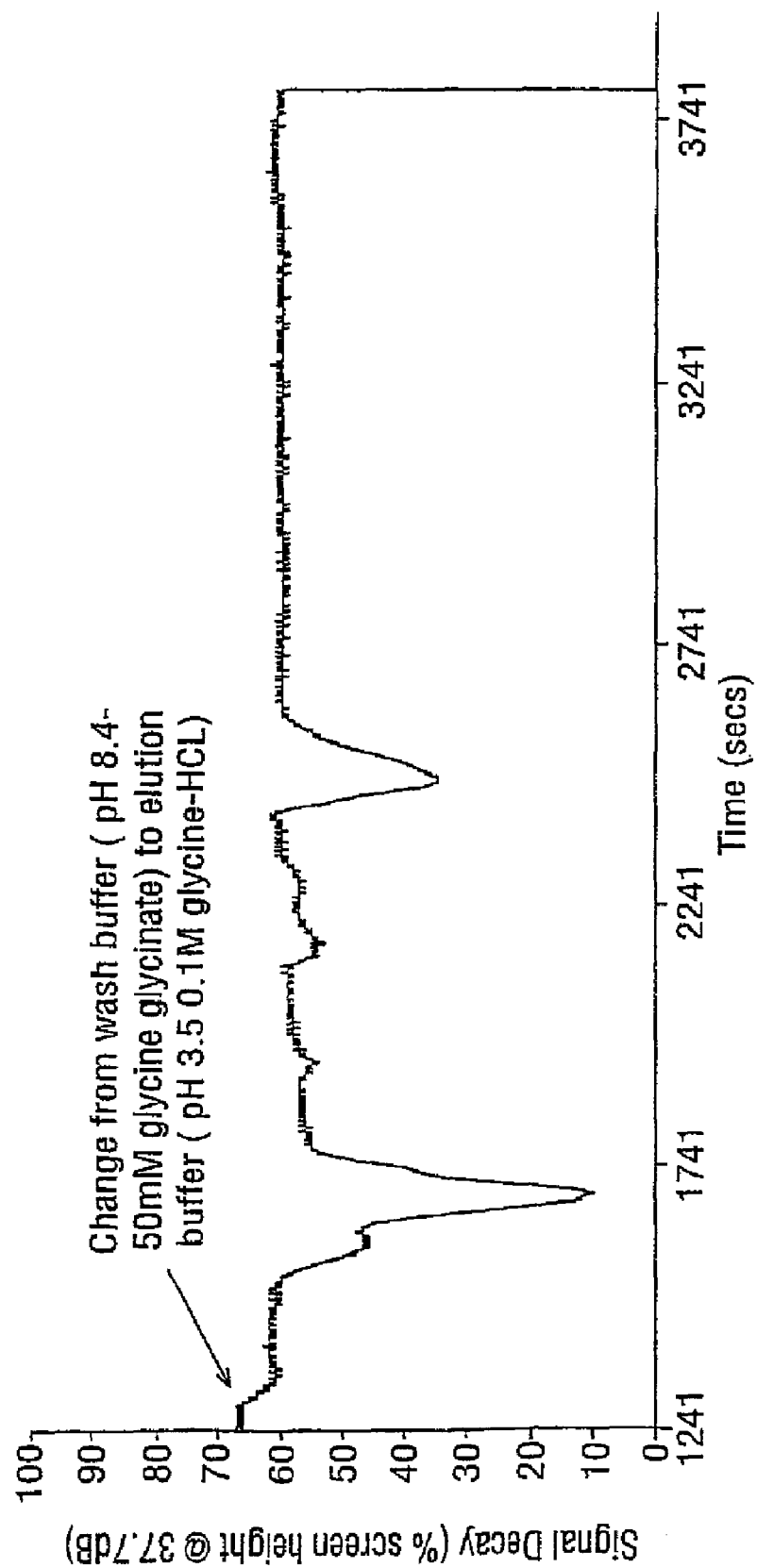

FIGS. 8 and 9 are supplementary data for the same run, explained in the legends on the figures.

Figure 10:
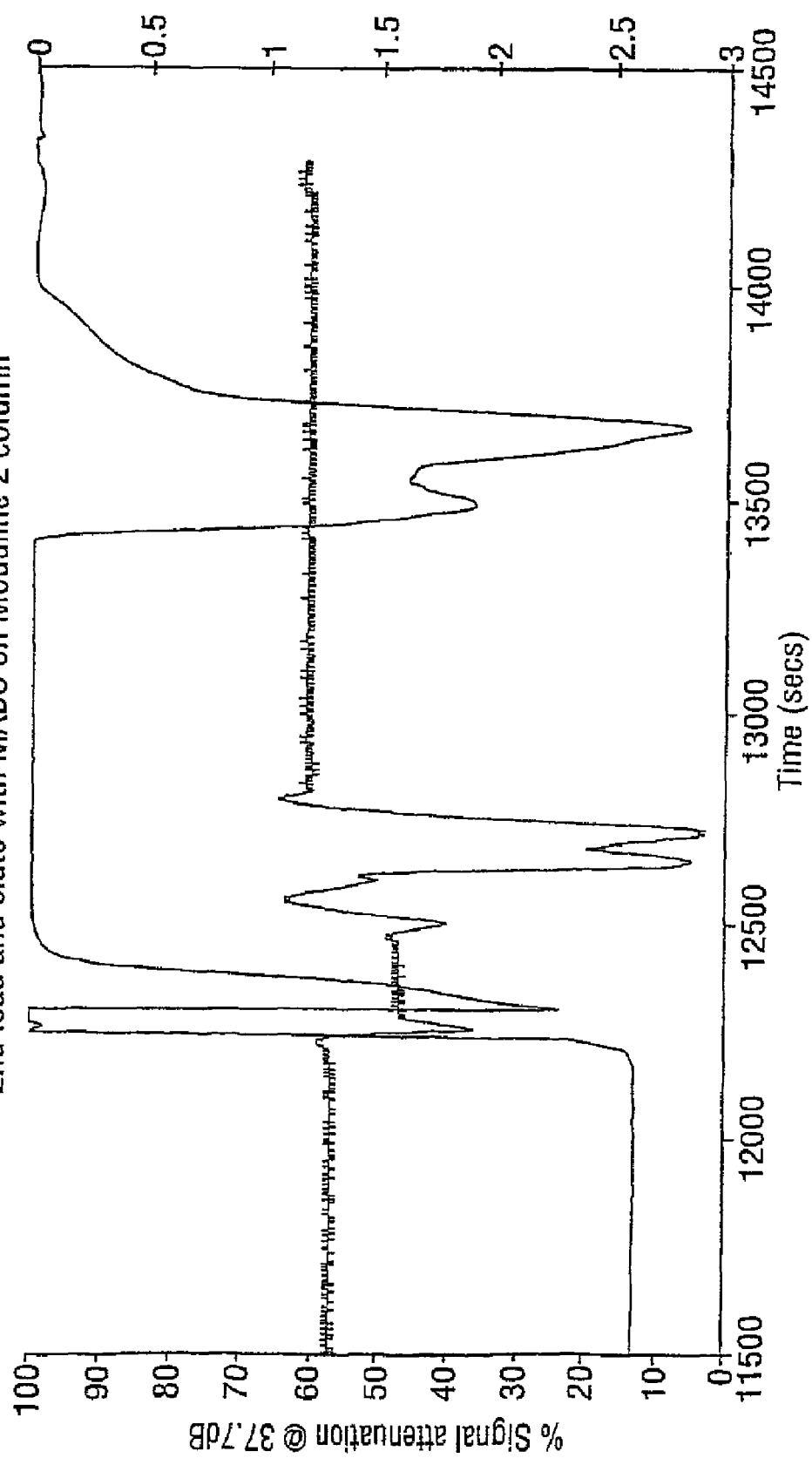

FIG. 10 shows a second run that loaded the column much more highly. Again the UV and ultrasound peaks are very similar (i.e. double peaks) with the ultrasound peak viewed before the UV.

These experiments show that the ultrasound equipment can retrieve both qualitative and quantitative data from within a column packed with media, under usage conditions with commercially important molecules.

Apparatus Proposals

Figure 11:
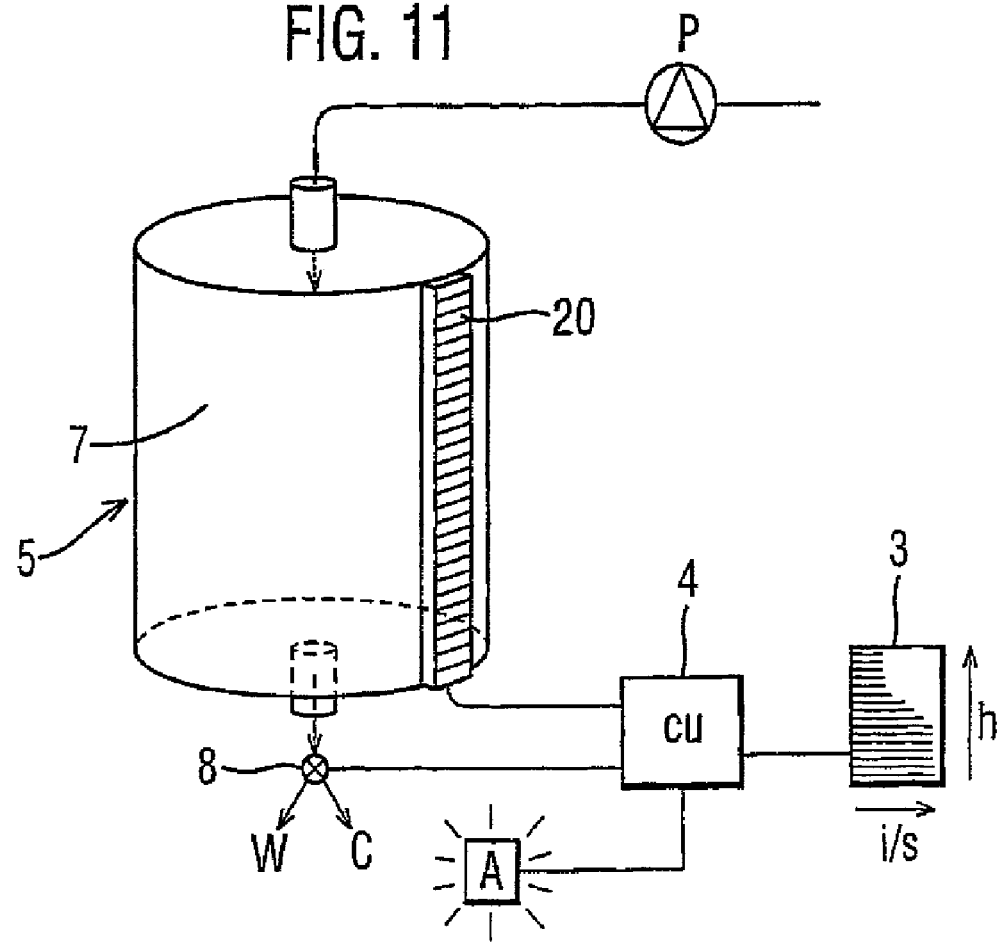
FIGS. 11 and 12 illustrate schematically a multi-transceiver array on a column, with a control processor, alarm and display used in a chromatography run.
Figure 12:
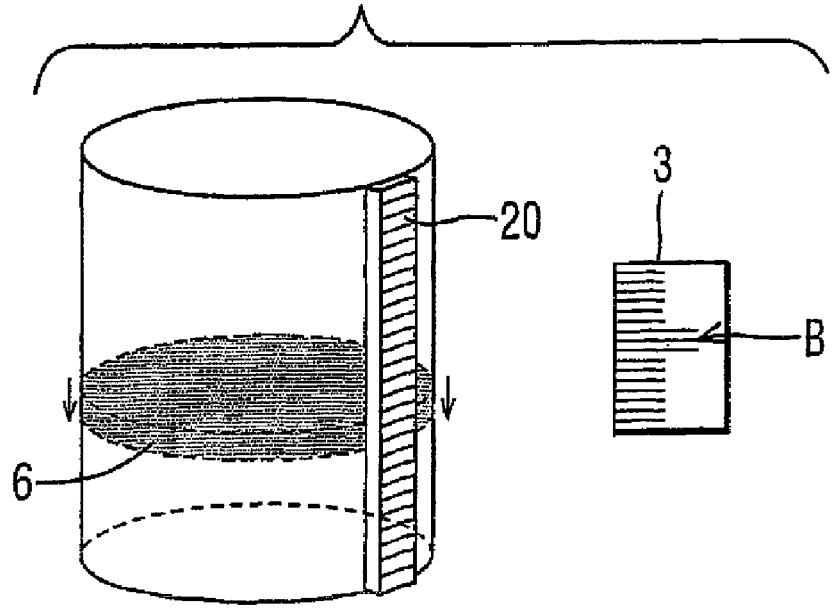

FIG. 11 shows schematically a chromatography process set-up, with an array of multiple ultrasound transceivers 20 installed right up the side wall 7 of the column 5. Output from the transceivers 20 is fed to respective inputs of a process control unit 4, preferably a programmed logic controller chip, which is connected in turn to drive a display 3 (indicating pictorially the presence of peaks etc. in the column interior according to axial position h), an alarm "A" which is sounded when comparison of prevailing actual conditions with pre-loaded model conditions reveals a mismatch above a permissible level, and/or when the sensor indicates (see FIG. 12) that a band 6 of a target substance is nearing the outlet at the bottom of the column, and a connection to the operating driver for a switching valve 8 which switches output from the column between a collecting line C and a waste line W.

Figure 13:
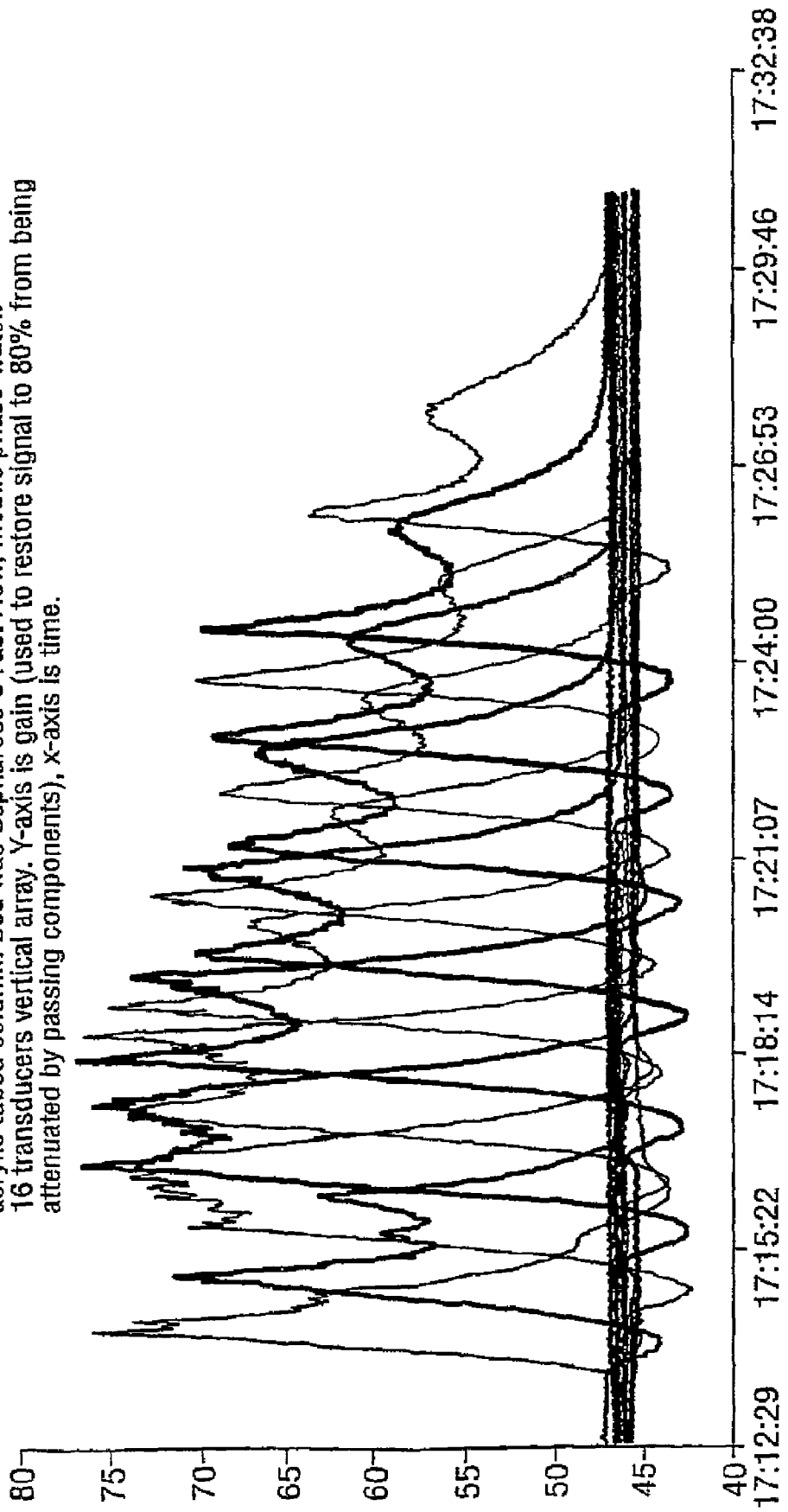
FIG. 13 shows the outputs from a sixteen-transceiver array as an injection of acetone is passed through a column.

FIG. 13 shows output actually obtained with a multi-sensor array. This was a 400 mm diameter column, 310 mm bed height, the bed Sepharose 6 fast flow, the mobile phase water. Sixteen piezoelectric ultrasound transducers supplied by Agfa were secured against the outside wall of the column in a vertical array. The Y-axis is gain (used to restore the detected signal to 80% of the original strength, and therefore indicating the degree of attenuation by passing through the column) while the X-axis is time. The mobile phase was water, and the detected component was a 1.5 litre injection of 1% acetone. The data indicate the passage of the acetone peak past the respective transceivers, the distinctive shape of the acetone peak and the gradual spreading as it moves down the column.

FIG. 14 shows schematically a portable transceiver array 2, consisting of a plastics unit 23 with sixteen individual transceivers 201 extending vertically—in this embodiment they are staggered to accommodate their dimensions—and having securing straps 26 to hold the concave front face 22 of the array housing 23 firmly against the outside wall of a corresponding column. A communication cable 25 carries the power and signals to and from the transducers 201.

FIG. 15 shows a refinement, with the front of the transducer housing 23 being recessed to provide an internal cavity 35. The contoured front edge 31 of the housing has a seal gasket 32 so that, with the housing clamped against the column side wall 7, an enclosed chamber is formed. This can be filled with water or other suitable liquid 28 through a top fill opening 29. This is found to be useful in enabling the zeroing of the multiple transducers 201, avoiding difficulties which otherwise arise in getting precise matching of the solid-solid interfaces between transducer and column wall.

The invention claimed is:

1. A method of operating a chromatography apparatus, the apparatus comprising a chromatography column with a housing wall having a side wall and end portions defining an internal bed space to contain a particulate chromatography medium, comprising passing ultrasound signals through the bed space and detecting the transmitted signals to determine the status of materials in the bed space, and using the detected signals in one or more of the following:
   (i) determining whether a component eluting through the particulate material in the bed space satisfies a predetermined profile characteristic for such a component, and if it does not, initiating a warning signal;
   (ii) detecting the imminent arrival of an eluting component at the outlet of the column, and initiating the operation of a collecting valve at the column outlet, which switches the output from one line to another;
   (iii) comparing the overall column transmission characteristics with a predetermined threshold value to determine whether the material in the column is fit for use;
   (iv) initiating a warning signal when the impending arrival of a component to be collected is detected adjacent the column outlet;
   (v) monitoring and indicating or displaying the passage of a front between different mobile phase liquids along the column; and,
   (vi) indicating the degree of expansion of particulate media in an expanded-bed chromatography process.

2. The chromatography method according to claim 1 including transmitting ultrasound signals through the bed space along plural transmission paths distributed axially along the column.

3. The chromatography method according to claim 2 including separating a component of interest, wherein the component is a product of a biological culture process.

4. The chromatography method according to claim 1 including separating a component of interest, wherein the component is a product of a biological culture process.

5. The chromatography method according to claim 1, including using the detected signals in two or more of (i) through (vi).

6. The chromatography method according to claim 1, including using the detected signals in three or more of (i) through (vi).

7. The chromatography method of claim 1, including eluting a component through the particulate material in the bed space, wherein the component comprises a protein.

8. The chromatography method of claim 1, including eluting a component through the particulate material in the bed space, wherein the component comprises an immunoglobulin.

9. The chromatography method of claim 8 wherein the immunoglobulin is a monoclonal antibody.

10. A method of operating a chromatography apparatus, the apparatus comprising a chromatography column with a housing wall having a side wall and end portions defining an internal bed space to contain a particulate chromatography medium, comprising passing ultrasound signals through the bed space and detecting the transmitted signals to determine the status of materials in the bed space, and using the detected signals in one or more of the following:
   (i) determining whether a component eluting through the particulate material in the bed space satisfies a predetermined profile characteristic for such a component, and if it does not, initiating a warning signal;
   (ii) detecting the imminent arrival of an eluting component at the outlet of the column, and initiating the operation of a collecting valve at the column outlet, which switches the output from one line to another;
   (iii) initiating a warning signal when the impending arrival of a component to be collected is detected adjacent the column outlet; and
   (iv) monitoring and indicating or displaying the passage of a front between different mobile phase liquids along the column.

11. The chromatography method according to claim 1, including using the detected signals in two or more of (i) through (iv).

12. A method of operating a chromatography apparatus, the apparatus comprising a chromatography column with a housing wall having a side wall and end portions defining an internal bed space to contain a particulate chromatography medium, comprising passing ultrasound signals through the bed space and detecting the transmitted signals to determine the status of materials in the bed space, and using the detected signals in one or more of the following:

(i) determining whether a component eluting through the particulate material in the bed space satisfies a predetermined profile characteristic for such a component, and if it does not, initiating a warning signal;

(ii) detecting the imminent arrival of an eluting component at the outlet of the column, and initiating the operation of a collecting valve at the column outlet, which switches the output from one line to another;

(iii) comparing the overall column transmission characteristics with a predetermined threshold value to determine whether the material in the column is fit for use;

(iv) initiating a warning signal when the impending arrival of a component to be collected is detected adjacent the column outlet; and (v) monitoring and indicating or displaying the passage of a front between different mobile phase liquids along the column.

* * * * *